United States Patent [19]

Russo

[11] Patent Number: 5,255,676

[45] Date of Patent: * Oct. 26, 1993

[54] SAFETY SEALED TRACHEAL SUCTION SYSTEM

[76] Inventor: Ronald D. Russo, 8 Candleberry Rd., Barrington, R.I. 02806

[*] Notice: The portion of the term of this patent subsequent to Jan. 28, 2009 has been disclaimed.

[21] Appl. No.: 789,315

[22] Filed: Nov. 8, 1991

[51] Int. Cl.⁵ ............................................. A61M 16/00
[52] U.S. Cl. ........................... 128/207.14; 128/207.16; 128/912; 128/205.24; 604/119; 604/905
[58] Field of Search ............. 128/202.16, 207.14, 128/207.15, 207.16, 207.17, 205.12, 205.19, 200.24, 912, DIG. 26, 205.24; 604/119, 171, 173, 192, 284, 905, 118, 43, 44, 45

[56] References Cited

U.S. PATENT DOCUMENTS

| | | | |
|---|---|---|---|
| 3,902,492 | 9/1975 | Greenhalgh . | |
| 3,902,500 | 9/1975 | Dryden | 128/207.14 |
| 3,912,795 | 10/1975 | Jackson | 128/207.14 X |
| 4,062,363 | 12/1977 | Bonner | 604/171 |
| 4,240,417 | 12/1980 | Holever | 128/207.15 X |
| 4,351,328 | 9/1982 | Bodai | 128/207.14 X |
| 4,510,933 | 4/1985 | Wendt et al. | 128/207.14 |
| 4,634,433 | 1/1987 | Osborne | 604/171 |
| 4,638,539 | 1/1987 | Palmer | 128/207.16 X |
| 4,649,914 | 3/1987 | Kowalewski | 128/207.15 |
| 4,669,463 | 6/1987 | McConnell | 128/207.14 |
| 4,827,925 | 5/1989 | Vilasi | 128/207.14 |
| 4,850,350 | 7/1989 | Jackson | 604/119 X |
| 4,967,743 | 11/1990 | Lambert | 128/207.16 X |
| 5,029,580 | 7/1991 | Radford et al. | 128/207.14 |
| 5,083,561 | 1/1992 | Russo | 128/207.16 |
| 5,088,486 | 2/1992 | Jinotti | 128/912 X |

Primary Examiner—V. Millin
Assistant Examiner—Sebastiano Passaniti
Attorney, Agent, or Firm—Robert J. Doherty

[57] ABSTRACT

A unitized ventilating system with front, side, and rear swivel connections and a sealed suction catheter assembly permitting continuous ventilation of a patient and combined suctioning ability. The entry ports to the assembly are normally valved closed to prevent the escape of vitally needed ventilating gases to atmosphere when the system is attached to the ventilator. The catheter is housed in a pre-formed collapsible protective envelope subassembly with attached couplings for convenient inexpensive manufacturing assembly. The entire system is designed for patient safety, healthcare worker protection from infectious diseases, simplified manufacturing, reduced cost, and completely disposable after twenty-four hours of continuous use.

12 Claims, 4 Drawing Sheets

SAFETY SEALED TRACHEAL SUCTION SYSTEM

BACKGROUND OF THE INVENTION

The use of single use disposable suction catheters to remove accumulated sputum and mucous from a patient's airway is well known and widely used. These catheters require sterile handling of the device as by using protective gloves to protect the user from infectious diseases.

Endotracheal suctioning usually requires disconnecting the ventilator breathing circuit from the patient. Not having to disconnect the ventilator to suction the patient has many medical benefits. These benefits are described in great detail in the prior art first disclosed in the devices of Dryden, U.S. Pat. No. 3,902,500, and Bodai in U.S. Pat. No. 4,351,328.

Further, a multitude of closed suction and ventilating devices which do not require ventilation circuit disconnection have been disclosed including U.S. Pat. No. 3,991,762 to Radford; U.S. Pat. No. 4,850,350 to Jackson; U.S. Pat. Nos. 4,696,296 and 4,638,539 to Palmer; U.S. Pat. No. 4,838,255 to Lambert; and U.S. Pat. No. 4,805,611 to Hodgkins. All the devices described in the above patents use an irrigation port located at the distal end of the device and accessing the outside of the catheter. In addition, all such devices have normally closed suction control valves with mechanisms which obstruct fluid flow.

All these devices also have a removable closure cap on the irrigation port which, if left open, can permit vital administered ventilator oxygen to escape to atmosphere. The patient can be deprived of this oxygen if the user forgets to close the irrigation port cap. The device of Palmer, U.S. Pat. No. 4,696,296, has been commercialized, but it is very expensive, presently selling at over $15 to the hospital compared with a sterile disposable suction catheter including gloves at only $0.50 each. Accordingly, most hospitals reserve the Palmer device for only the most critically ill patients in the intensive care units and require that the rest of the patients use the cheaper disposable suction catheters.

Most recently, the present applicant in pending U.S. patent application Ser. No. 07/538,250 discloses a closed tracheal suction device with a proximally located irrigation port which accesses the inside of the catheter and a normally closed suction control valve permitting unobstructed improved fluid flow. This advanced Russo device, while considerably less costly to produce than that of Palmer, is, however, still moderately expensive. The presently disclosed invention, however, presents a device of modified construction which produces the same improved results as the above referred to Russo device but at a significantly lower manufacturing cost. Accordingly, the present Russo invention provides a device with all the features of Palmer with additional safety and performance features for both the patient and healthcare worker at a much reduced cost enabling far greater use and distribution of the device to all patients.

BRIEF SUMMARY AND OBJECTS OF THE INVENTION

With the foregoing in mind, the present invention offers a much safer and comfortable device for the patient. The lavage valve port is formed by a normally closed pre-slit diaphragm valve. During operation of the ventilator, no vital oxygen can be inadvertently lost to atmosphere because there is no potentially open passageway to atmosphere such as a closure cap which can be left open.

The valve is designed to withstand even the highest oxygen pressure rate which can be administered by the ventilator machine and not leak. It can only be opened by a luer tip irrigation syringe or a luer tip prefilled irrigation squeeze bottle. The valve is normally sealed closed and can only be opened by the luer tip. Upon removal of the luer tip, the valve positively seals closed again.

Front and side swivels are able to rotate 360 degrees to eliminate most stress applied to the patient's indwelling endotracheal tube by the ventilator circuitry tubing. The rear swivel also moves a full 360 degrees to always permit upright location of the lavage port and suction control valve regardless of whether the side swivel is located on the right or left of the patient's bed for connection to the ventilator machine.

The suction catheter is housed in a pre-formed collapsible envelope with a front and rear coupling as part of this subassembly. This catheter envelope coupling subassembly is rapidly, permanently attachable to the rear swivel at its distal end and to the one piece combination resilient molded lavage valve and suction control valve at it proximal end.

The suction control valve takes the form of a pre-slit integrally molded diaphragm which is manually deformable to provide an opening larger than the lumen of the suction catheter to maximize fluid flow efficiency.

Accordingly, it is a primary object to provide a closed tracheal suction system which is safer and more comfortable for the patient.

Another objective of the invention is to provide a completely sealed closed tracheal suction system preventing the user from coming in contact with any potentially infectious body fluids during use.

Another objective is to positively prevent the loss of any administered ventilator oxygen to atmosphere when the system is not in use.

Another objective is to reduce the number of components and labor to assemble the device to an absolute minimum to provide an improved device at the lowest possible cost.

It is another object of the invention to provide the lowest cost device making it available to all patients who could benefit from its use.

It is another object of the invention to have a lavage port valve and a suction control valve formed as part of a one piece inexpensive resilient molded component.

It is another object of the invention to provide a lavage valve port which can both provide bronchial lavage and be used to thoroughly flush the outside and inside of the catheter and the suction control valve and fluid passageways.

It is another objective of the invention to provide a device which provides maximum suction efficiency to prevent clogging and to thoroughly remove viscous mucous from a patient's airway.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DETAILED DESCRIPTION OF THE PREFERRED EMBODIMENT

Figure 1:
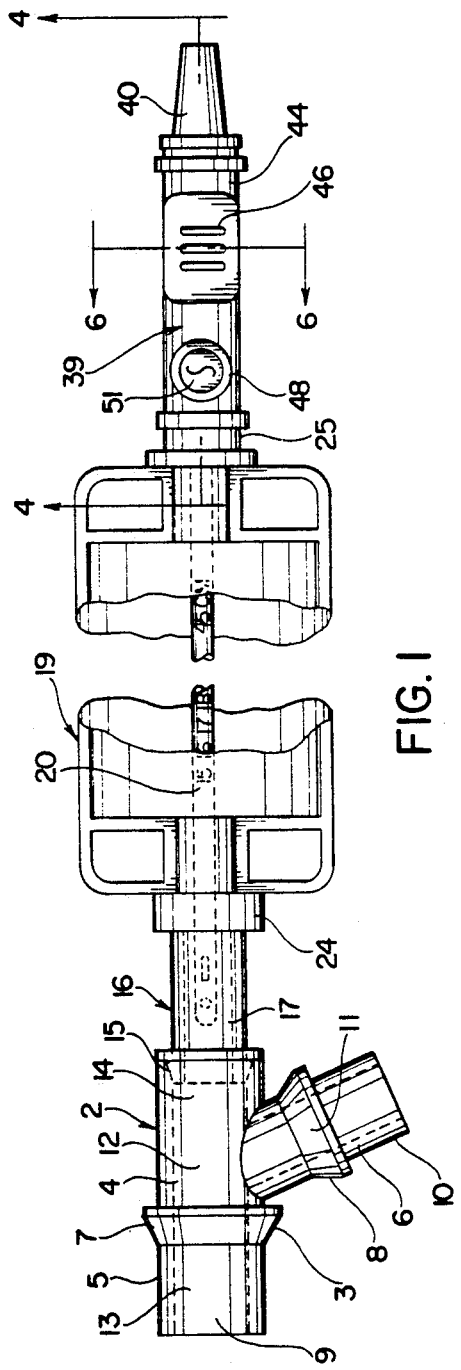
FIG. 1 is a top view of the present invention.

Referring in detail to the drawings, there is shown in FIG. 1 the closed tracheal suction system 2 including a frontal swivel adapter 3. The swivel adapter has a body 4 into which front swivel 5 is snap fit into body 4. Side swivel 6 is also snap fit into body 4. The body and both swivels are preferably injected molded of rigid thermoplastic typically polypropylene.

Front swivel 5 can rotate freely 360 degrees at flared joint 7 on the body. Likewise, side swivel 6 can rotate freely 360 degrees at flared joint 8. Both joints are lightly lubricated with medical grade silicone grease during snap fit assembly. Internal fitment 9 on the front swivel accepts any endotracheal tube directly attached to the patient's airway. External fitment 10 on the side swivel accepts any standard ventilator breathing circuit for the delivery of oxygen through the side swivel passageway 11 through body passageway 12 onto front swivel internal passageway 13 and then directly into the endotracheal tube and the patient's airway.

Body passageway 12 exits rearward at opening 14. Snap fit at joint 15 in opening 14 is a rigid visually clear housing 16 preferably injection molded of rigid PVC plastic. Joint 15 is an internal swivel joint also assembled with silicone grease such that housing 16 can rotate 360 degrees freely in relationship to body 4. Clear housing 16 is formed with an internal chamber 17 which directly communicates with body passageway 12. Press fit into the rear of housing 16 is cup seal 18 molded of resilient synthetic rubber typically Kraton.

Figure 2:
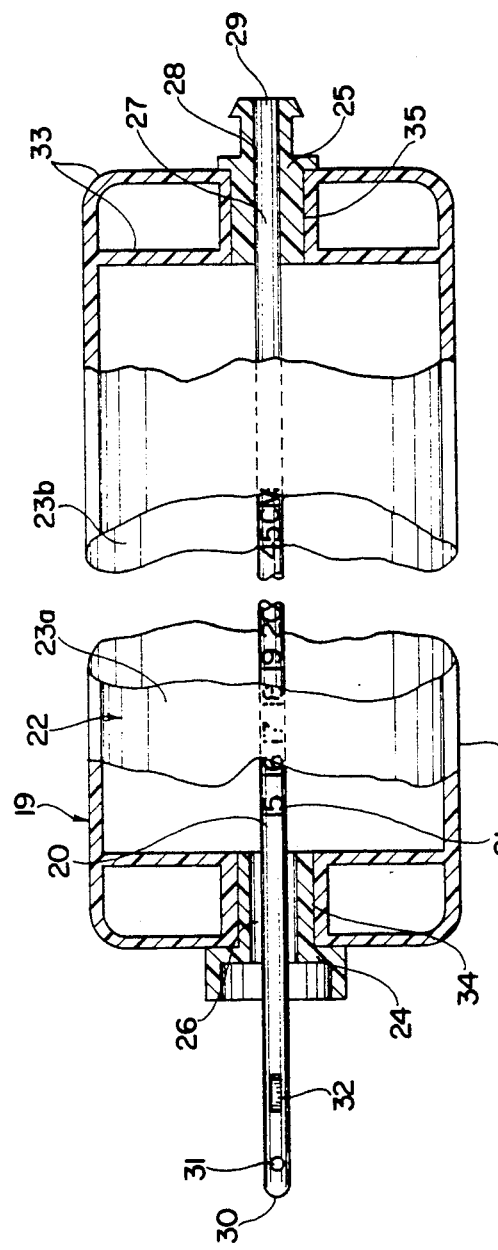
FIG. 2 is an enlarged partial sectional view of the catheter with collapsible envelope with the front and rear couplings subassembly.

Attached to housing 16 is preformed catheter envelope subassembly 19. Subassembly 19 is formed as a separate assembly shown in FIG. 2 in greater detail. Subassembly 19 includes a catheter 20 preferably made from extruded flexible PVC which is permanently ink pad printed with numerical centimeter graduations 21 starting with 15 cm up to 45 cm. The envelope 22 includes a front film 23a preferably of a vinyl 3 mil. taffeta finish and a rear film 23b also of vinyl 3 mil. finish. Attached to the front end of the envelope 22 is semi-rigid injection molded coupling 24 and rear injection molded coupling 25 both preferably molded from PVC vinyl attached to the rear of the envelope. The front of the catheter extends through passageway 26 in front coupling 24. The rear end of the catheter 27 is permanently attached as by solvent cementing into the rear coupling 25 at joint 28.

The catheter is typically a 14 FR size in the adult version of the system. A 14 FR catheter has an internal lumen 29 of 0.130 inches which extends from rear opening 29 all the way through to the distal opening 30 of the catheter. At the distal end of the catheter is side vent spray hole 31 and inked indicator mark 32.

The catheter envelope subassembly 19 is preferably fabricated in the following manner: First, the rear coupling with the catheter already solvent cemented in place is fixtured such that the catheter extends through front coupling passageway 26. Both the rear coupling with catheter attached and the front coupling with the catheter extending through it are fixtured down into the rear vinyl film 23b. Front vinyl film 23a is positioned on top of the rear vinyl film 23b. The front and the rear films are then RF (radio frequency) welded together along RF seal 33 which runs along the entire periphery of the envelope and also RF seals front coupling at RF weld joint 35. In its finished form, the rear coupling with catheter, the front coupling, and the front and rear film are instantaneously RF welded as one integral unit. The RF seal can take various configurations as desired. Also, the terms front and rear as applied to the films 23a and 23b could just as aptly be designated top and bottom since what is present prior to welding are two plastic sheets that are then superposed relative to each other and then fuse bonded along their peripheral contacting portions as well as along interior portions as dictated by the product design.

Since both couplings are vinyl along with the front and rear film, an excellent welded leakproof subassembly 19 accomplished. The subassembly method is fast, neat, and completely leakproof. It is extremely efficient and very inexpensive in that it eliminates all the labor intensive assemblies of the prior art. The catheter will move freely in and out of passageway 26 as the envelope is collapsed or retracted.

Figure 3:
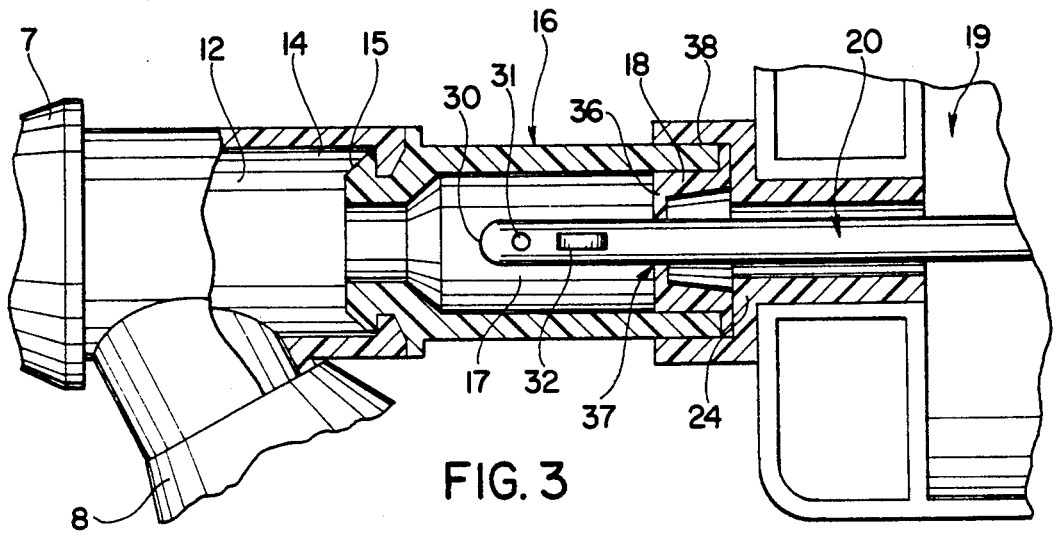
FIG. 3 is an enlarged partially sectional view of the catheter envelope subassembly attached to the rear swivel connector.

FIG. 3 shows the subassembly 19 connected to housing 16. As previously noted, cup seal 18 is lightly press fit into the rear of housing 16. The cup seal has a thin 0.015 inch thick diaphragm 36 through which is a molded inner hole 37 which is 0.120 inches in diameter to form a seal around 0.130 inch diameter catheter 20. During assembly, solvent cement is applied to the housing front coupling joint 38. The catheter is next inserted into hole 37 and front coupling 24 forms a solvent press fit at joint 38. The entire subassembly 19 is permanently joined to housing 16 in seconds.

The catheter envelope subassembly is permanently connected to both a swivel connection at its distal end and to a combination one piece resilient molded suction control valve and lavage valve port at its proximal end. The lavage valve port permits direct access to the catheter lumen permitting bronchial washing when the catheter is advanced into the patient's airway. The lavage valve port also permits total flushing of the fluid flow passageway of the catheter and the suction control valve to prevent clogging.

The catheter can be manually advanced through the envelope into the housing 16 and into body passageway 12 and into the patient's endotracheal tube and retracted as desired. Referring back to FIG. 1, a one piece resilient molded lavage valve port and suction control valve assembly 39 is shown attached to rear coupling 25. Fitted into valve assembly 39 is a suction connector 40. This assembly is shown cross sectioned in FIG. 4. The valve assembly is preferably molded in one piece of 60 durometer high tear strength medical grade silicone.

Figure 4:
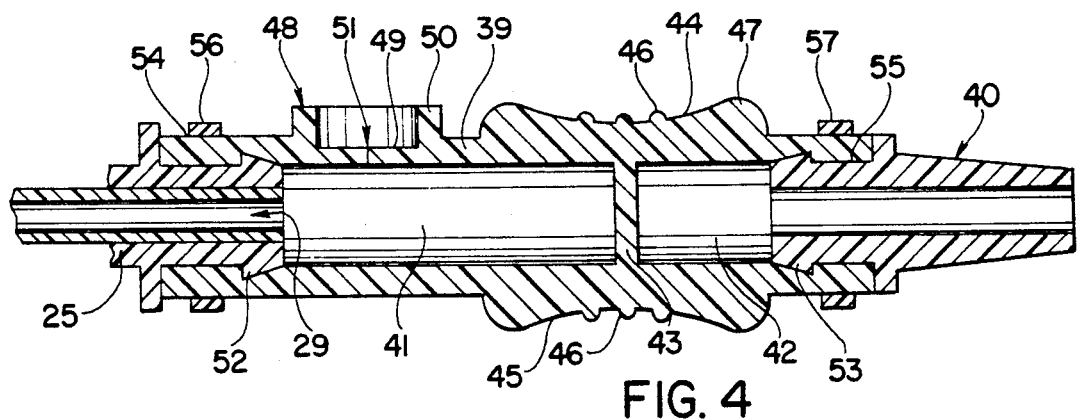
FIG. 4 is a cross-sectional view of the lavage port valve and suction control valve of FIG. 1 taken along line 4—4 of FIG. 1.
Figure 8:
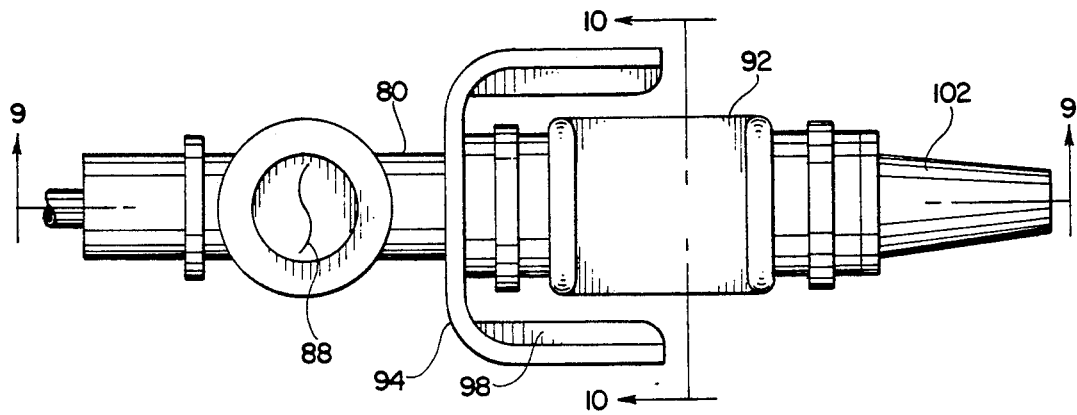
FIG. 8 is a top view of an alternate embodiment of the suction control valve and lavage port.

In FIG. 4, the valve assembly is shown including a front chamber 41 and a rear chamber 42. Transversing both chambers is integrally molded valve diaphragm 43 about 0.040 inches thick. Directly on top of diaphragm 43 is a molded-in thumb rest 44 and a finger rest 45 is molded underneath diaphragm 43. Cushion lines 46 are molded-in on both thumb and finger rests. Molded on top of the valve assembly 39 is lavage port valve 48 which also has a thin molded-in diaphragm 49 also 0.040 inches thick. Lavage valve port 48 is shaped in the form of a raised circular ring 50 into which is cut a manually deformable slit 51, e.g., an S-shaped slit. This S slit may be formed by punching using a mandrel with a punch die. It is preferable that the S slit be oriented generally at right angles (normal) to the linear axis of valve assembly 39 as shown in FIG. 8 since this orientation of the slit forms an excellent resilient seal and is believed to reduce any tendency of the slit to accidentally partially open by bending or twisting of the assembly 39 along its longitudinal axis as can happen during use. It should be pointed out that the slit may take other forms in addition to S-shaped, i.e., Z-shape, squiggly line, or even straight or I-shaped so long as the seal and deformable characteristics are met.

Attachment of the one-piece assembly 39 to the rear coupling 25 and suction connector 40 is fast and permanent. Rear coupling 25 has a molded-in barb 52 and connector 40 also has a molded-in barb 53. Connector 40 is injection molded of rigid polypropylene. Front passageway 41 is a slightly press fit over barb 52 on rear coupling 25 at circular joint 54. Rear passageway 42 is also slightly press fit over connector barb 53 at circular joint 55. Nylon snap ring bands 56 and 57 permanently lock in both ends of assembly 39 onto rear coupling 25 and connector 40. Once assembled, front passageway 41 is in direct communication with the lumen 29 of catheter 20 as shown in FIG. 4.

Figure 5:
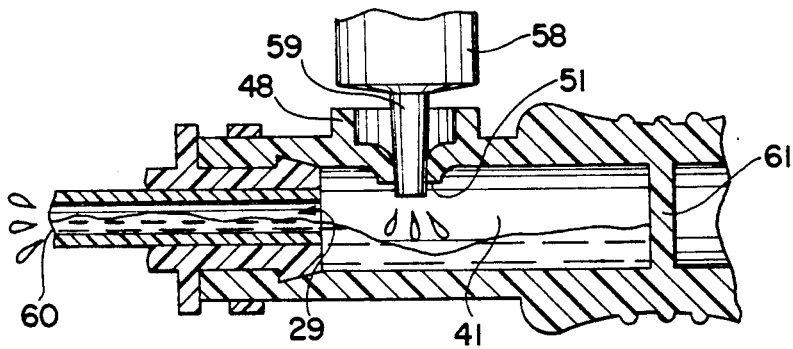
FIG. 5 is a cross-sectional view of the lavage valve port portion of the device including a luer tip irrigating syringe with flushing fluid.

FIG. 5 shows an irrigating syringe 58 with luer tip 59 entering into S slit 51 on lavage valve port 48. Irrigating fluid can enter into passageway 41 and into catheter lumen 29 moving forward into catheter internal flow path 60. When bronchial lavage is desired, the catheter can simply be advanced into the patient's airway about 6 inches and about 5 mls of irrigating fluid such as saline is squirted into the lavage valve. Irrigating fluid will squirt out the distal tip 30 of the catheter to lavage the bronchus. Retraction of the luer tip irrigating syringe will automatically seal the lavage valve closed.

Figure 6:
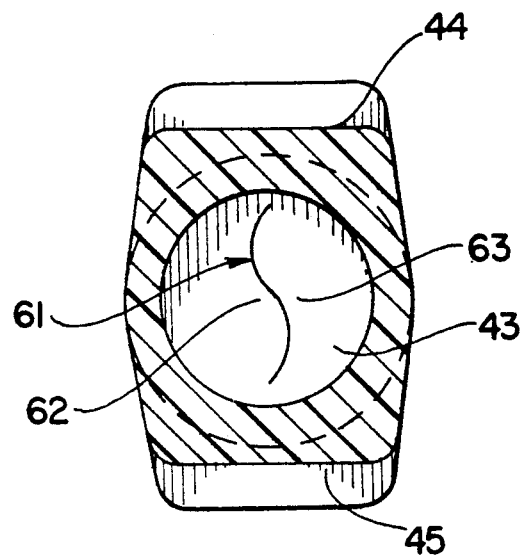
FIG. 6 is a cross-sectional view of the suction control valve in a normally closed position of the device of FIG. 1 taken along line 6—6 thereof.
Figure 7:
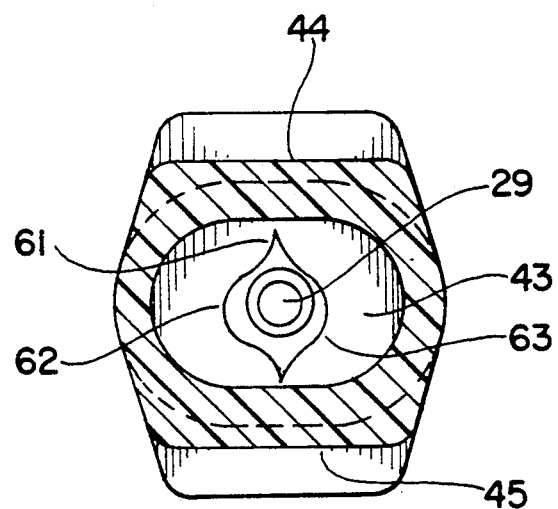
FIG. 7 is a cross-sectional view of the suction control valve manually depressed in an open position.

FIG. 6 shows the molded-in suction control valve in a cross-sectional view normally closed. Diaphragm 43 is pierced with a vertical S slit 61. The S slit forms a left leaf 62 and a right leaf 63 which are sealed shut when the valve is in its normally closed position. When suction is desired, the valve is manually depressed at thumb rest 44 and finger rest 45. FIG. 7 shows the valve depressed open thus parting leafs 62 and 63 to form an opening preferably larger than the catheter lumen 29. It should also be pointed out that the depicted shape of that portion of the valve assembly 39 which houses diaphragm 43 assists in preventing the accidental opening of diaphragm 43 as by a patient rolling over onto the assembly or by laying an arm or hand thereon. In this regard, the opposed raised or enlarged ends 47 tend to cooperatively form a platform upon which an arm or hand can rest without squeeze contacting the central portions of the assembly opposite the diaphragm 43, that is, to say the opposed thumb and finger rest or contact areas 44 and 45 respectively.

Should, however, a more positive guard feature be desired for the system, then such may be provided. In that regard, reference is made to FIGS. 8-10. FIG. 8 showing an alternate embodiment of the combination suction control valve and lavage port. There is shown an injection molded valve housing 80 which has a central passageway 82 into which the suction catheter is solvent cemented in place. A side port 84 is molded into the housing which accesses the central passageway. Press fit into the side port is silicone molded lavage port valve 86 which has a S slit valve opening 88. Lavage or irrigation solution can be administered into the lavage port through the S slit. Press fitting the lavage port valve into the side port enables the S slit to be biased closed so it is not necessary to orient the S slit in any position in relationship to the valve housing. The valve housing has a molded-in rear fitting 90 which permits connection of a separate one piece molded silicone suction control valve 92. Also molded into the housing is a protective valve guard 94 which partially surrounds the suction control valve. The guard has an upwardly extending end wall 96 which in turn supports side walls 98 which partially envelope, and side walls 96 which rise above the top surface 100 of the suction control valve much in the way the guard of a sword handle functions. The purpose of the guard is to prevent accidental depression of the suction control valve if the patient were to roll over on the valve or rest a hand or arm thereon.

Figure 9:
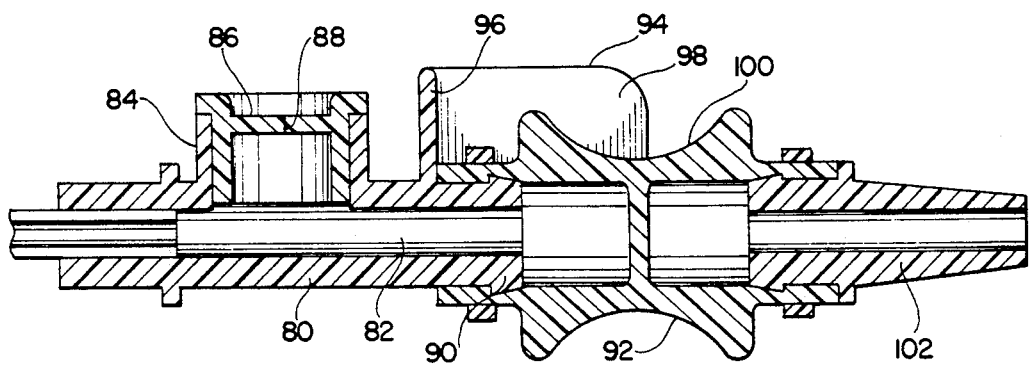
FIG. 9 is a cross-sectional view of FIG. 8 taken along lines 9—9.
Figure 10:
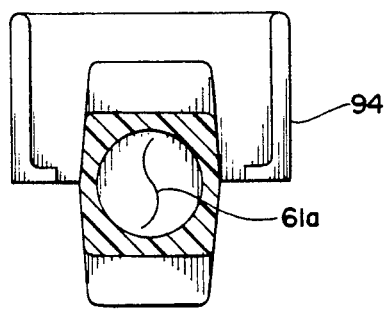
FIG. 10 is a cross-sectional view of FIG. 8 taken along lines 10—10.

A suction connector 102 is attached to the rear of the valve for easy connection to a source of suction. Cross-sectional FIG. 9 shows these elements in detail. FIG. 10 shows the S slit valve 61a within the suction control valve. The side walls of the valve guard are also shown in FIG. 10.

It should thus be apparent that the valve housing 80 of the FIGS. 8-10 embodiment differs from that of assembly 39 in that it is two piece rather than one piece and that the portion that holds the lavage port is of a stiff plastic material. This relative stiffness of the separate piece 80 not only enables the guard 94 to be formed therewith but also enables a wider selection of lavage port configurations to be possible. Other than the above, the assembly of FIGS. 8-10 operates in the same manner as previously described.

The connection 40 is connected to a source of vacuum through flexible connecting tubing when suction is desired. To suction the patient, the catheter is advanced manually through the envelope into the patient's airway and the suction control valve depressed intermittently by squeezing the thumb and finger engaging areas 44 and 45 while the catheter is being withdrawn slowly. After suctioning, the catheter is fully retracted until indicator mark 32 is clearly visible through clear housing 16.

To flush the entire fluid passageway after suctioning, irrigation fluid (about 15 mls) is applied through the lavage port. This flushing fluid will flush out through both catheter opening 30 and vent spray hole 31 into catheter internal rinsing chamber 17 in housing 16 as shown in FIG. 3. Depression of the suction control valve will flush out rinsing fluid from chamber 17 and the entire fluid passageway of the device. After flushing, the connecting tube is disconnected from the suction connector and the entire system remains completely sealed ready for its next suctioning or bronchial lavage procedure.

At no time during any of the procedures does the healthcare worker come in contact with any of the aspirated body fluids. In addition, the entire system remains sealed to prevent the escape of vital oxygen when the catheter is not in use. The entire assembly is designed for ease of assembly and low cost production. It can be sterile packaged, ready for single patient use, and its lower cost will make it available to more patients. The entire assembly is designed to be disposed after 24 hours use along with the disposable breathing circuit on the ventilator.

While there is shown and described herein certain specific structures embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A combination irrigation port valve and suction control valve assembly comprising: a front inner passageway including an opening connected to a conduit, said conduit capable of delivering either suction or infusion of a fluid, an irrigation port valve in fluid communication with the front inner passageway and conduit and the port valve always in a normally closed position except when it is engageably opened by irrigation fluid for infusion and the valve automatically returning to its normally closed position when irrigation fluid is removed, a proximal end opening on the inner passageway in fluid communication with a normally closed one piece resiliently molded suction control valve which is manually deformable to an open position and the suction control valve returning to its normally closed position when the suction control valve is not manually deformed and the suction control valve further connectable to a source of suction to the inner passageway and conduit when the suction control valve is deformed open and both said irrigation port valve and said suction control valve being capable of acting independently of each other to either apply irrigation fluid or suction to the passageway and conduit, said irrigation port valve housed within a rigid assembly formed as a separate piece from the suction control valve and said suction control valve formed as a one piece resilient component with a manually deformable diaphragm, said assembly including a guard portion for preventing accidental depression of the suction control valve.

2. The assembly of claim 1 wherein both valves are manually deformable diaphragms with pre-slits for opening and closing.

3. The assembly of claim 1 wherein the conduit is a suction catheter.

4. The assembly of claim 1 wherein the assembly is used as part of a closed tracheal suction system.

5. The assembly of claim 1 wherein the irrigation port valve is housed within a rigid assembly formed as a separate piece from the suction control valve and said suction control valve is formed as a one piece resilient component with a manually deformable diaphragm.

6. The assembly of claim 1, said guard portion rearwardly extending over a portion of said suction control valve assembly.

7. A combination irrigation port valve and suction control valve assembly for use with and in combination with a closed patient ventilation and suction catheter device connectable to a patient's airway permitting suctioning as needed, said combination assembly comprising a front inner passageway including an opening connected to a conduit, said conduit capable of delivering either suction or infusion of a fluid, an irrigation port valve in fluid communication with the front inner passageway and conduit and the port valve always in a normally closed position except when it is engageably opened by irrigation fluid for infusion and the valve automatically returning to its normally closed position when irrigation fluid is removed, a proximal end opening on the inner passageway in fluid communication with a normally closed one piece, resiliently-molded diaphragm suction control valve which is manually deformable to an open position and the suction control valve returning to its normally closed position when the suction control valve is not manually deformed and the suction control valve further connectable to a source of suction to the inner passageway and conduit when the suction control valve is deformed open and both said irrigation port valve and said suction control valve being capable of acting independently of each other to either apply irrigation fluid or suction to the passageway and conduit, and said assembly including a guard portion for preventing accidental depression of the suction control valve.

8. The assembly of claim 7, said irrigation port valve including said guard portion, said guard portion rearwardly extending over a portion of said suction control valve.

9. In combination with a medical device which is capable of applying suction to a patient by the operation of said device, a valve assembly comprising a one piece resiliently deformable body having front and rear ends and a longitudinal passageway extending therethrough and open at its rear end and means at the rear end of said body for receiving a source of suction and open at the front end and means at the front end of said body for connecting a means for accessing a patient with said suction source, said body including outside wall portions and an integral diaphragm extending across said passageway and normally closing said passageway and further dividing said passageway into a rear chamber and a front chamber, said rear chamber including said body rear end for receiving said suction source, said diaphragm movable to an open position by the manual application of external force to opposite outside wall portions of said body.

10. The assembly of claim 9 including an irrigation port permitting installation of irrigation solution into said passageway.

11. The assembly of claim 10 wherein both the irrigation port and suction control valve are integral and proximal to said means for receiving a source of suction.

12. The assembly of claim 9, including a guard portion for preventing accidental depression to said opposite outside wall portions of said body.

* * * * *